(12) United States Patent
Hummel, Jr. et al.

(10) Patent No.: US 7,263,710 B1
(45) Date of Patent: Aug. 28, 2007

(54) MEDICAL DIAGNOSTIC SYSTEM WITH ON-LINE REAL-TIME VIDEO TRAINING

(75) Inventors: Henry John Hummel, Jr., Waukesha, WI (US); Thomas L. Lamoureux, Waukesha, WI (US); Karamjeet Singh, Germantown, WI (US); Sunil Melepatt Palliyal, Waukesha, WI (US); David Adam Ross, Wauwatosa, WI (US); James F. Kohli, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/477,042

(22) Filed: Dec. 31, 1999

(51) Int. Cl.
*H04N 7/173* (2006.01)
*H04N 7/18* (2006.01)
*H04N 7/16* (2006.01)
*G09B 23/28* (2006.01)
*G09B 7/00* (2006.01)
*A61B 5/00* (2006.01)

(52) U.S. Cl. .................... 725/86; 725/25; 725/74; 725/82; 434/262; 434/323; 600/300

(58) Field of Classification Search .......... 725/86–100, 725/105, 2, 30, 25, 104, 3, 74, 82; 434/323, 434/262; 600/300
See application file for complete search history.

(56) References Cited

U.S. PATENT DOCUMENTS

| | | | | |
|---|---|---|---|---|
| 5,609,485 A | * | 3/1997 | Bergman et al. | 434/262 |
| 5,619,249 A | * | 4/1997 | Billock et al. | 725/5 |
| 5,791,907 A | * | 8/1998 | Ramshaw et al. | 434/262 |
| 5,867,821 A | * | 2/1999 | Ballantyne et al. | 705/2 |
| 5,872,915 A | * | 2/1999 | Dykes et al. | 726/5 |
| 5,878,746 A | * | 3/1999 | Lemelson et al. | 128/653.1 |
| 6,063,030 A | * | 5/2000 | Vara et al. | 600/437 |
| 6,184,878 B1 | * | 2/2001 | Alonso et al. | 345/327 |
| 6,409,661 B1 | * | 6/2002 | Murphy | 600/300 |
| 6,434,572 B2 | * | 8/2002 | Derzay et al. | 707/104.1 |
| 6,449,001 B1 | * | 9/2002 | Levy et al. | 348/14.08 |
| 6,477,708 B1 | * | 11/2002 | Sawa | 725/116 |
| 6,684,400 B1 | * | 1/2004 | Goode et al. | 725/61 |

* cited by examiner

*Primary Examiner*—Chris S. Kelley
*Assistant Examiner*—Joseph G Ustaris
(74) *Attorney, Agent, or Firm*—Ostrager Chong Flaherty & Broitman P.C.

(57) ABSTRACT

A central service facility is connected via a network and a uniform service interactive platform to a multiplicity of remotely located medical diagnostic systems. The interactive platform includes a video/audio plug-in application which can be used to access a library of videos via a network. The video library is stored at the central service facility or on a local area network at the remote facility. The interactive platform of the medical diagnostic system comprises a web browser which enables the end-user to search and select a training video from the database, and a video/audio player for viewing the selected video directly from the operator's console. Depending on bandwidth availability, the video file can be downloaded to the remotely located medical diagnostic equipment prior to display or streamed in real-time.

5 Claims, 7 Drawing Sheets

MEDICAL DIAGNOSTIC SYSTEM WITH ON-LINE REAL-TIME VIDEO TRAINING

FIELD OF THE INVENTION

The present invention relates generally to the field of medical diagnostic systems. More particularly, the invention relates to a diagnostic system having a user interface which facilitates obtaining services from a service provider via a network.

BACKGROUND OF THE INVENTION

Medical diagnostic systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computerized tomography (CT) systems, x-ray systems (including both conventional and digital or digitized imaging systems), magnetic resonance imaging (MRI) systems, positron emission tomography (PET) systems, ultrasound systems, nuclear medicine systems, etc. In many instances, these modalities complement one another and offer the physician a range of techniques for imaging particular types of tissue, organs, physiological systems, etc. Health care institutions often arrange several such imaging systems at a single or multiple facilities, permitting its physicians to draw upon such resources as required by particular patient needs.

Modern medical diagnostic systems typically include circuitry for acquiring image data and for transforming the data into a useable form, which is then processed to create a reconstructed image of features of interest within the patient. The image data acquisition and processing circuitry is sometimes referred to as a "scanner" if physical or electronic scanning occurs as part of the imaging process. The particular components of the system and related circuitry, of course, differ greatly between modalities due to their different physics and data processing requirements.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly without the need for intervention on the part of the institution personnel. Such centralized servicing is intended to maintain the diagnostic systems in good operational order without necessitating the attention of physicians or radiologists, and is often quite transparent to the institution.

In certain centralized servicing systems, a computerized service center may contact a scanner via a network to check system configurations and operational states, to collect data for report generation, and to perform other useful service functions. Such contacts can be made periodically, such as during system "sweeps", in which a variety of system performance data is collected and stored with historical data for the particular scanner. The data can then be used to evaluate system performance, propose or schedule visits by service personnel, and the like.

In addition, currently available service systems also permit some degree of interaction between service centers and institutions. For example, an interactive service system is known which facilitates valuable exchanges of information, including reports of system performance, feedback on particular incidents requiring attention, updates of system licenses, software, imaging protocols, etc. In particular, a platform has been developed that serves as a base for the interactive servicing needs of different modalities. This platform allows a central service facility to exchange information on possible service problems with remotely located scanners of different modalities, and to retrieve information or data log files from scanners for the purpose of servicing those scanners. The platform provides a uniform interface permitting clinicians and radiologists to operate a variety of scanners, and to report service issues for the scanners, via a uniform, intuitive format.

The known integrated user-interactive platform for servicing diagnostic equipment at remote locations may be configured in software, hardware, or firmware at the scanner or may be installed in a central operator's station linking several scanners in a medical facility. The user interface permits service requests to be generated prior to, during or subsequent to examinations executed on the diagnostic equipment. The user interface also permits service messaging, report generation and retrieval, etc. The user interface is preferably configured as a network browser, which also facilitates linking the scanner or the central facility control station to a network such as an intranet or internet. The same user interface may be integrated into scanners of different modalities, thereby further facilitating service requests and the like by operations personnel, without requiring the personnel to become reacquainted with diverse interfaces in a facility.

The existence of a uniform service interactive platform for facilitating interactive communication between remote medical facilities and a central service facility via a network provides a means for educating and training end-users in the use of diagnostic systems at the remote facilities. In particular, the end-users can be instructed regarding complex tasks and procedures, such as how to use specific features of a diagnostic system to perform specific tasks. The use of a network to educate and train end-users can improve both productivity and patient care. In addition, the dissemination of common information throughout a networked system of remote facilities would further the goal of standardizing examination procedures.

SUMMARY OF THE INVENTION

The present invention is directed to a system comprising a multiplicity of remotely located medical diagnostic systems and workstations, a central video library and a uniform service interactive platform which enables an end-user at a remote diagnostic system or workstation to search, select and view a video from the central library. The interactive platform includes a video/audio plug-in application which can be used to access a library of videos via a network. In accordance with one preferred embodiment, the video library is stored at a central service facility and is accessed from a remote diagnostic system or workstation via the uniform service interactive platform and an intranet. In accordance with another preferred embodiment, the video library is stored at the central service facility and is accessed from a workstation (e.g., a personal computer) at the remote facility via the Internet. In accordance with a further preferred embodiment, the video library is stored on a local area network at the remote facility and is accessed from diagnostic systems and workstations via the uniform service interactive platform. The interactive platform of the medical diagnostic system comprises a web browser which enables the end-user to search and select a training video directly from the operator's console. The interactive platform further comprises a video/audio player for viewing the selected video at the operator's console of the diagnostic system or at the workstation. Depending on bandwidth availability, the video file can be downloaded to the diagnostic system or workstation prior to display or can be streamed to the diagnostic system or workstation in real-time.

The present invention is also directed to a method for providing on-line real-time video training at any one of a multiplicity of networked medical diagnostic systems and/or workstations. The diagnostic systems may include different imaging modalities, such as ultrasound, x-ray and computerized tomography scanners. Preferably the video library comprises training videos showing how to operate the scanning equipment, how to perform patient examinations or how make diagnoses for each imaging modality.

In accordance with the preferred embodiments of the invention, the uniform service interactive platform comprises a web page formatted to provide a graphical user interface for searching and selecting a training video from the video library. Preferably the videos in the library are classified by imaging modality.

The present invention supplies training videos on demand to end-users in real-time. For example, in the case of an end-user who is scheduled to perform a particular procedure on a particular diagnostic system, prior to the scheduled appointment the end-user can search the library for a video teaching how to perform that procedure, select the appropriate video from the library and then view the selected video at the operator's console in real-time. Alternatively, the end-user can sit at a nearby station which is equipped with a personal computer for searching, selecting and viewing a training video.

Figure 1:
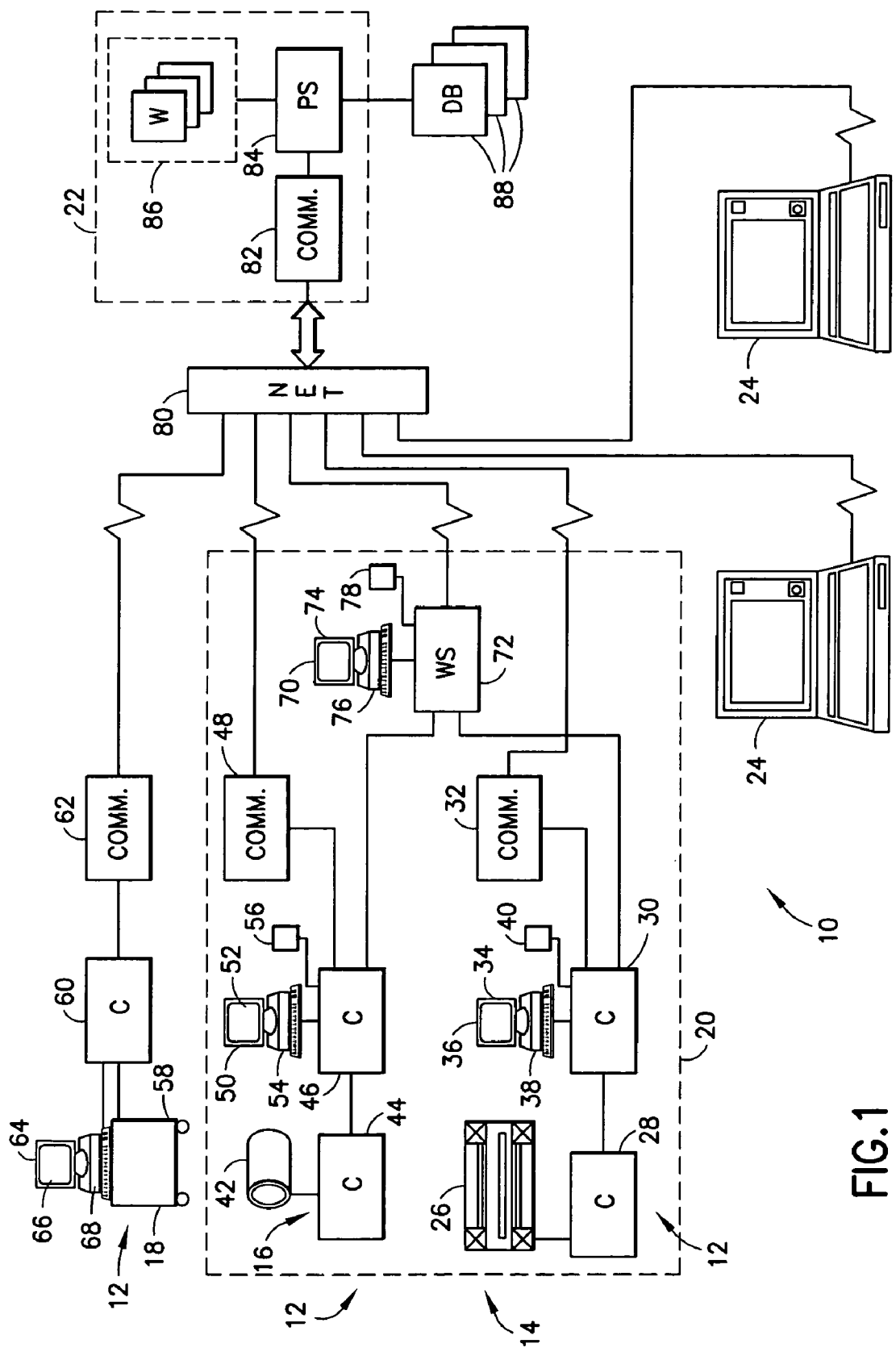
FIG. 1 is a diagrammatical representation of a series of medical diagnostic systems coupled to a service facility via a network connection for providing centralized service and data interchange between the diagnostic systems and the service facility.

Reference characters not explicitly defined in a figure are understood to be the same as in prior figures, where applicable.

DETAILED DESCRIPTION OF THE PREFERRED EMBODIMENTS

Referring to FIG. 1, a service system 10 is illustrated for providing centralized service to a plurality of remotely located medical diagnostic systems 12. In the embodiment shown in FIG. 1, the medical diagnostic systems include an MRI system 14, a CT system 16, and an ultrasound imaging system 18. The diagnostic systems may be positioned in a single location or facility, such as a medical facility 20, or may be remote from one another as shown in the case of ultrasound system 18. The diagnostic systems are serviced from a centralized service facility 22. Moreover, a plurality of field service units 24 may be coupled in the service system for transmitting service requests, verifying service status, transmitting service data etc. as described more fully below.

In the system shown in FIG. 1, several different system modalities are provided with central service by the service facility. These and other modalities may be similarly serviced by the service facility, depending upon the capabilities of the service facility, the types of diagnostic systems subscribing to service contracts with the facility, as well as other factors. In general, however, the system shown in FIG. 1 is well suited to providing central service to a wide variety of medical diagnostic system modalities, including but not limited to MRI, CT, ultrasound imaging, PET, and nuclear medicine systems. Moreover, the various modality systems serviced may be of different type, manufacture and model. Service requests and data transmitted between the diagnostic systems and the service facility include data for identifying the type and modality of the serviced system, as well as data specifically adapted to the system modality and model. It should also be noted that, as used herein, the term "service request" is intended to include a wide range of inquiries, comments, suggestions and other queries or messages generated by a diagnostic system or an institution in which a system is disposed or managed. In particular, such requests may relate to problems occurring on systems, applications questions, questions of a general nature, questions relating to financial or subscription arrangements, information sharing, reports, applications, protocols, etc.

Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. System controller 30 includes a uniform platform for interactively exchanging service requests, messages and data with service facility 22 as described more fully below. System controller 30 is linked to a communications module 32, which may be included in a single or separate physical package from system controller 30. System controller 30 is also linked to an operator station 34, which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics. More particularly, equipment incorporating the service interface disclosed herein may include imaging systems, clinical diagnostic systems, physiological monitoring systems, etc.

Similarly, CT system 16 will typically include a scanner 42 which detects portions of x-ray radiation directed through a subject of interest. Scanner 42 is coupled to a generator and controller, as well as to a signal acquisition unit, represented collectively at reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for central service of system 16. Also, system controller 46 is coupled to an operator station 50 which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular design. In particular, in the case of ultrasound system 18, such systems will generally include a scanner and data processing unit 58 for transmitting ultrasound signals into a subject of interest, and for acquiring resultant signals which are processed for reconstructing a useful image. The system includes a system controller 60 which regulates operation of scanner 58 and which processes acquired signals to reconstruct the image. Moreover, system 18 includes a communications module 62 for transmitting service requests, messages and data between system controller 60 and service facility 22. System 18 also includes an operator station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. The management station may be linked directly to controllers for the various diagnostic systems, such as controllers 30 and 46 in the illustrated example. The management system may include a computer workstation or personal computer 72 coupled to the system controllers in an intranet configuration, a file-sharing configuration, a client/server arrangement, or any other suitable arrangement. Management station 70 will typically include a monitor 74 for viewing system operational parameters, analyzing system utilization, and exchanging service requests and data between the remote facility 20 and the central service facility 22. Input devices, such as a standard computer keyboard 76 and mouse 78, may also be provided to facilitate the user interface. It should be noted that, alternatively, the management system, or other diagnostic system components, may be stand-alone, i.e., not coupled directly to a diagnostic system. In such cases, the service platform described herein, and some or all of the service functionality may nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 72 and field service units 24, may be linked to service facility 22 via a remote access network 80. For this purpose, any suitable network connection may be employed. Preferred network configurations include both proprietary or dedicated networks, as well as open networks, such as the Internet. Data may be exchanged between the diagnostic systems, field service units 24, and central service facility 22 in any suitable format, such as in accordance with the Internet Protocol (IP), the Transmission Control Protocol (TCP), or other known protocols. Moreover, certain of the data may be transmitted or formatted via markup languages, such as the HyperText Markup Language (HTML), or other standard languages. The preferred interface structures and communications components are described in greater detail below.

Within service facility 22, messages, service requests and data are received by communication components as indicated generally at reference numeral 82. Components 82 transmit the service data to a service center processing system, represented generally at reference numeral 84 in FIG. 1. The processing system manages the receipt, handling and transmission of service data to and from the service facility. In general, processing system 84 may include one or a plurality of computers, as well as dedicated hardware or software servers for processing the various service requests and for receiving and transmitting the service data, as described more fully below. Service facility 22 also includes a bank of operator workstations 86, which may be staffed by service engineers who address the service requests and provide off- and on-line service to the diagnostic systems in response to the service requests. Also, processing system 84 may be linked to a system of databases or other processing systems 88 at or remote from the service facility 22. Such databases and processing systems may include extensive database information on operating parameters, service histories, etc., both for particular subscribing scanners and for extended populations of diagnostic equipment. As described below, such databases may be employed both for servicing of particular diagnostic systems and for tracking such servicing, as well as for deriving comparison data for use in servicing a particular system or a family of systems.

Figure 2:
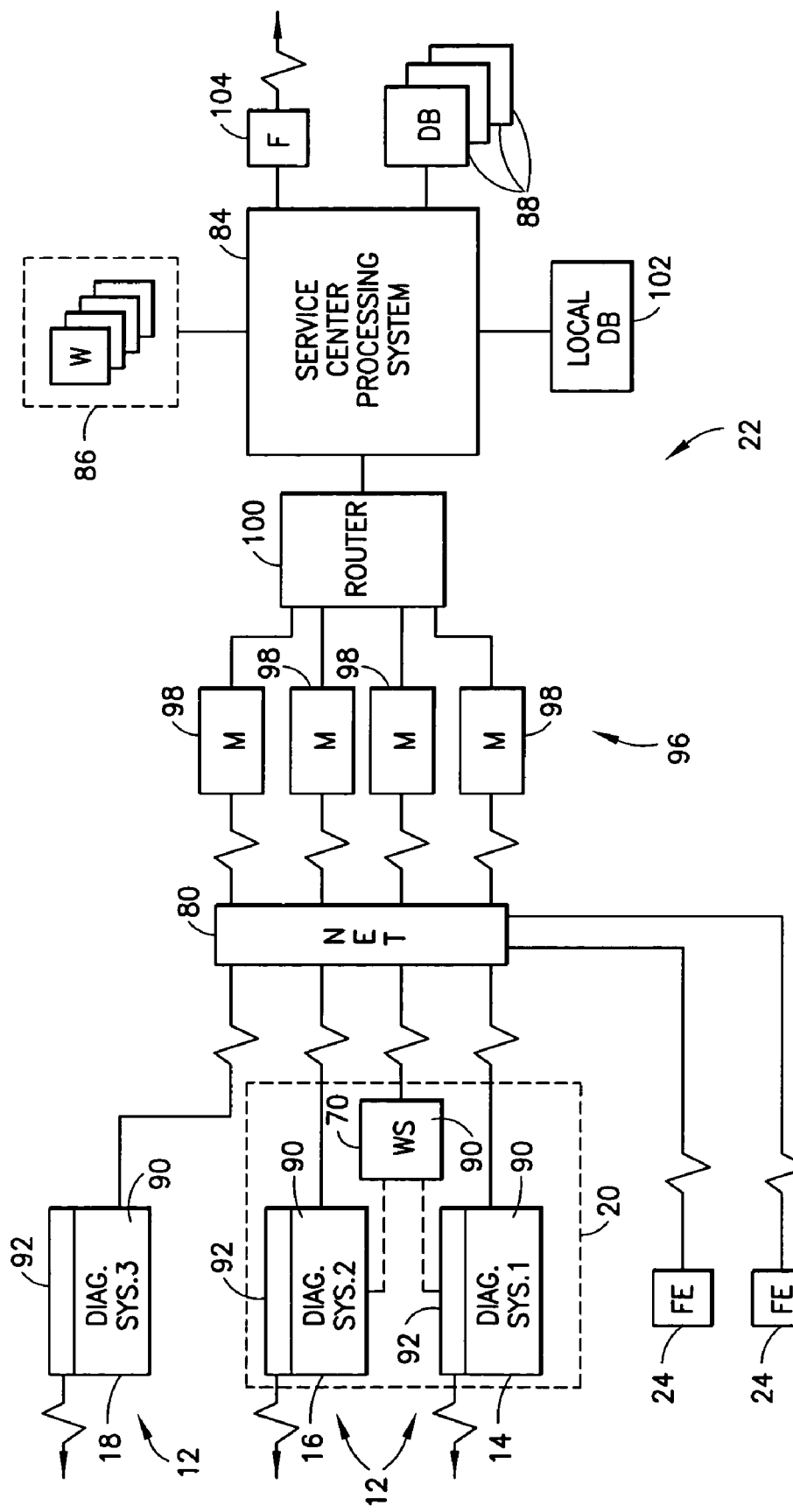
FIG. 2 is a block diagram of the systems shown in FIG. 1, illustrating certain functional components of the diagnostic systems and the service facility.

FIG. 2 is a block diagram illustrating the foregoing system components in a functional view. As shown in FIG. 2, remotely located field service units 24 and diagnostic systems 12 can be linked to the central service facility 22 via a network connection as illustrated generally at reference numeral 80. Within each diagnostic system 12, a uniform service platform 90 is provided. Platform 90, which is described in greater detail below with particular reference to FIG. 3, includes hardware, firmware, and software components adapted for composing and transmitting service requests and service task lists, transmitting and receiving service data, establishing network connections, and managing financial or subscriber arrangements between the diagnostic system and the service facility. Preferably, the platform 90 is integrated into the system controller of the diagnostic system. These platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 70 is provided, a similar uniform platform is preferably loaded on the management station to facilitate direct interfacing between the management station and the service facility. In addition to the uniform service platform 90, each diagnostic system is preferably provided with an alternative communications module 92, such as a facsimile transmission module for sending and receiving facsimile messages between the remotely located scanner and the central service facility.

Messages and data transmitted between the diagnostic systems and the service facility traverse a security barrier or "firewall" contained within processing system 84, which prevents unauthorized access to the service facility in a manner generally known in the art. A modem rack 96, including a series of modems 98, receives the incoming data, and transmits outgoing data through a router 100, which manages data traffic between the modems and the service center processing system 84.

As mentioned above, processing system 84 receives and processes the service requests and data, and interfaces with additional service components, both at the service facility and remote from the facility. As shown in FIG. 2, operator workstations 86 are coupled to the processing system, as are remote databases or computers 88. In addition, at least one local service database 102 is provided for verifying license and contract arrangements, storing service record files, log files, etc. Moreover, one or more communication modules 104 are linked to processing system 84 to send and receive facsimile transmissions between the service facility and the diagnostic systems or field service units.

Figure 3:
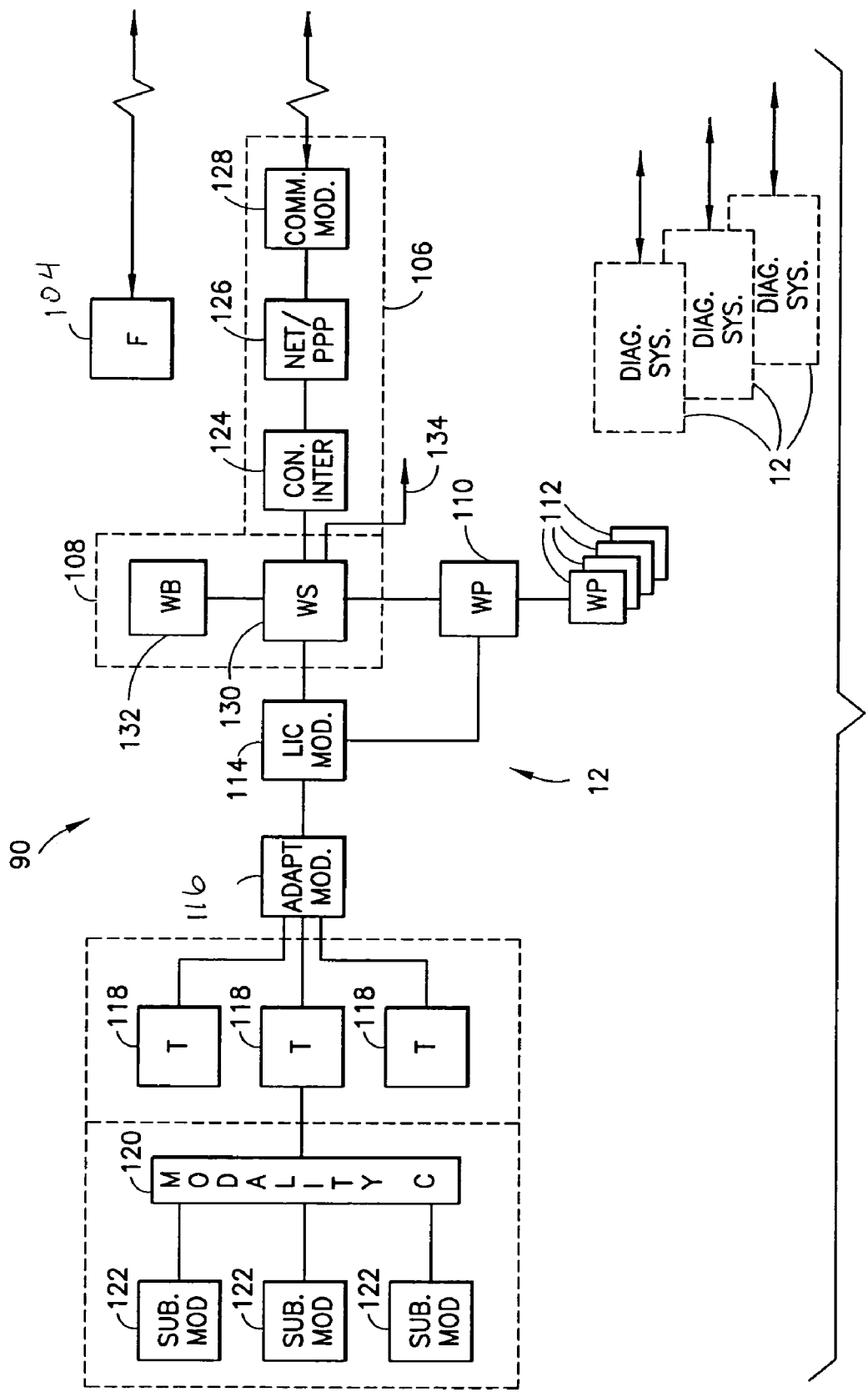
FIG. 3 is a block diagram of certain functional components within a diagnostic system of the type shown in FIGS. 1 and 2 for facilitating interactive centralized servicing of the diagnostic system.

FIG. 3 shows the various functional components comprising the uniform service platform 90 within each diagnostic system 12. The uniform platform includes a device connectivity module 106, as well as a web services connectivity module 108. Web services connectivity module 108 accesses a main web page 110 which, as mentioned above, is preferably a markup language page, such as an HTML page displayed for the system user on a monitor at the diagnostic system. Main web page 110 is preferably accessible from a normal operating page in which the user will configure examination requests, view the results of examinations, etc., such as via an on-screen icon. Through main web page 110, a series of additional web pages 112 are accessible. Such web pages permit service requests and requests for training videos to be composed and transmitted to the central service facility, and facilitate the exchange of other messages, reports, software, protocols, etc. as described more fully below. It should be noted that as used herein, the term "page" includes a user interface screen or similar arrangement which can be viewed by a user of the diagnostic system (or workstation), such as screens providing graphical or textual representations of data, messages, reports, etc. Moreover, such pages may be defined by a markup language or a programming language such as Java, perl, java script, or any other suitable language.

Web services connectivity module 108 is coupled to a license module 114 for verifying the status of the license, fee or contractual subscriptions between the diagnostic system and the service facility. As used herein, the term "subscription" should be understood to include various arrangements, contractual, commercial or otherwise for the provision of services, information, software, and the like, with or without payment of a fee. Moreover, the particular arrangements managed by systems as described below may include several different types of subscriptions, including time-expiring arrangements, one-time fee arrangements, and so-called "pay per use" arrangements, to mention but a few.

License module 114 is, in turn, coupled to one or more adapter utilities 116 for interfacing the browser, server, and communications components with modality interface tools 118. In a preferred configuration, several such interface tools are provided for exchanging data between the system scanner and the service platform. For example, modality interface tools 118 may include applets or servlets for building modality-specific applications, as well as configuration templates, graphical user interface customization code, etc. Adapters 116 may interact with such components, or directly with a modality controller 120 which is coupled to modality-specific subcomponents 122. The modality controller 120 and modality-specific subcomponents 122 will typically include a preconfigured processor or computer for executing examinations, and memory circuitry for storing image data files, log files, error files, etc. Adapter 116 may interface with such circuitry to convert the stored data to and from desired protocols, such as between the HyperText Transfer Protocol (HTTP) and DICOM, a standard for digital imaging communications. Moreover, transfer of files and data may be performed via any suitable protocol, such as a file transfer protocol (FTP) or other network protocol.

In the illustrated embodiment, device connectivity module 106 includes several components for providing data exchange between the diagnostic system and the central service facility. In particular, a connectivity service module 124 provides for interfacing with web services connectivity module 108. A Point-to-Point Protocol (PPP) module 126 is also provided for transmitting Internet Protocol (IP) packets over remote communication connections. Finally, a modem 128 is provided for receiving and transmitting data between the diagnostic system and the central service facility. As will be appreciated by those skilled in the art, various other network protocols and components may be employed within device connectivity module 106 for facilitating such data exchange.

Web services connectivity module 108 preferably includes a server 130 and a browser 132. Server 130 facilitates data exchange between the diagnostic system and the service facility, and permits a series of web pages 110 and 112 to be viewed via browser 132. In a preferred embodiment, server 130 and browser 132 support HTTP applications and the browser supports Java applications. Other servers and browsers or similar software packages may, of course, be employed for exchanging data, service requests, messages, and software between the diagnostic system and the central service facility. Finally, a direct network connection 134 may be provided between web server 130 and a local area network 174 (shown in FIG. 5) within the remote medical facility.

In a preferred embodiment, the components comprising web services connectivity module may be configured via an application stored as part of the uniform platform. In particular, a Java application licensed to a service engineer enables the engineer to configure the device connectivity at the diagnostic system to permit it to connect with the central service facility. Features of the application are segmented into separate tabbed pages accessible by the service engineer. The application is entered via a license agreement screen. Once accepted, the service engineer can configure parameters of the system modem, the schedule for running automatic diagnostic checks, and establish electronic messaging, such as for automatic service report generation. Once the modem is configured, the service engineer establishes contact with the service facility and provides data enabling the service facility to download any remaining data needed for secure communication between the diagnostic system and the service center. Upon exit from the application, a configuration status is presented to the service engineer, including status of an automatic test of connectivity between the sites.

Figure 4:
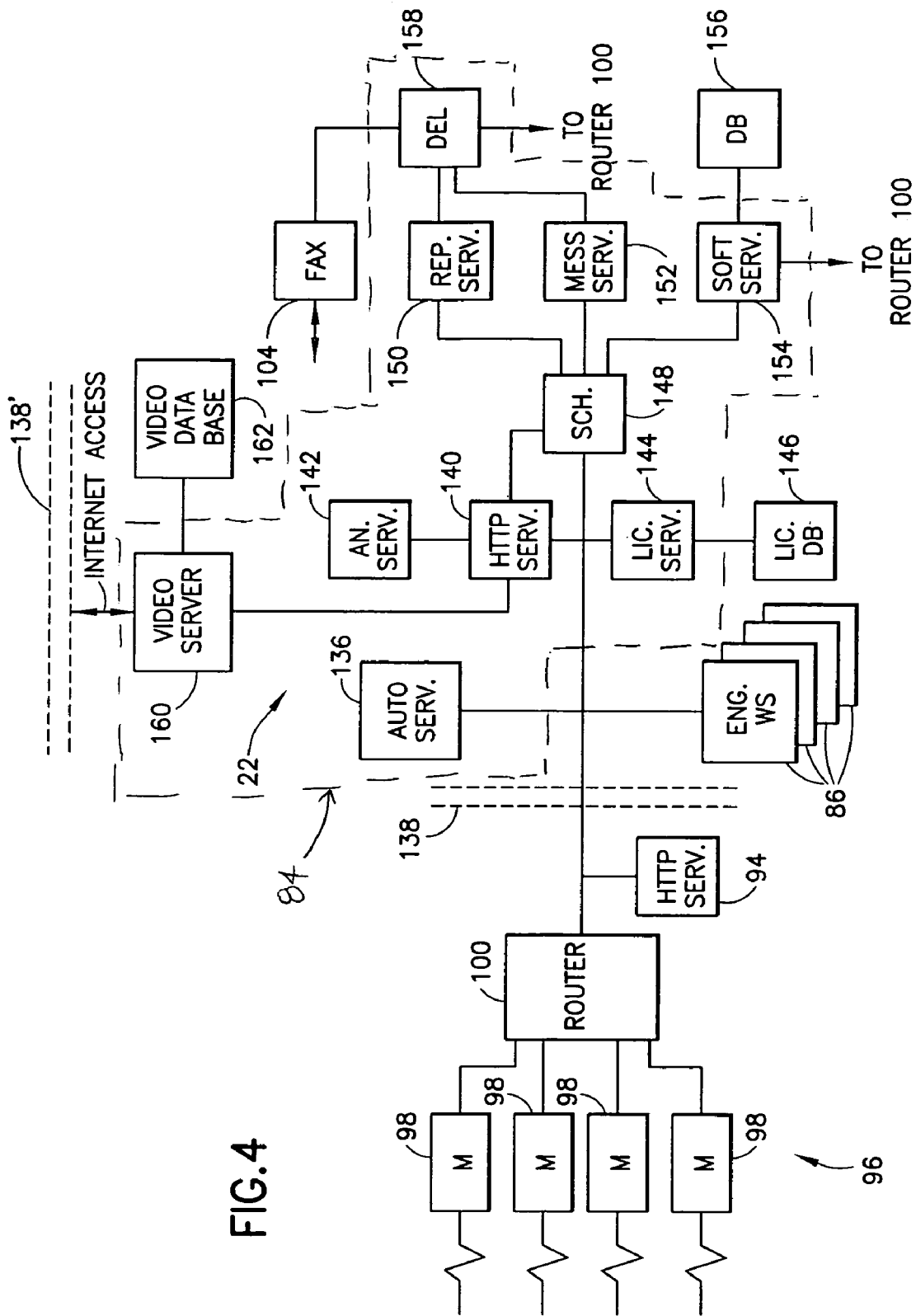
FIG. 4 is a block diagram of certain of the functional components of the service facility in accordance with the preferred embodiment of the invention for rendering interactive centralized service to a plurality of remotely located medical diagnostic systems.

FIG. 4 illustrates exemplary functional components for service facility 22. As indicated above, service facility 22 includes a modem rack 96 comprising a plurality of modems 98 coupled to a router 100 for coordinating data communications with the service facility. A so-called "front office" HTTP service server 94 receives and directs incoming and outgoing transactions with the facility. Server 94 is coupled to the other components of the facility through a firewall 138 for system security. Operator workstations 86 are coupled to the port manager for handling service requests and transmitting messages and reports in response to such requests. An automated service unit 136 may also be included in the service facility for automatically responding to certain service requests, sweeping subscribing diagnostic systems for operational parameter data, etc. In a preferred embodiment, the automated service unit 136 may operate independently of or in conjunction with the interactive service components comprising processing system 84. It should be noted that other network or communications schemes may be provided for enabling the service facility to communicate and exchange data and messages with diagnostic systems and central service units, such as systems including outside Internet service providers and virtual private networks.

Behind firewall 138, a so-called "back office" HTTP application server 140 coordinates handling of service requests, requests for training videos, messaging, reporting, software transfers, etc. Other servers may be coupled to HTTP application server 140, such as service analysis servers 142 configured to address specific types of service requests, and video server 160 configured to address requests for training videos. In response to a request for a training video from a subscriber, the video server 160 retrieves the video/audio data for the requested video from the video database 162 and transmits that video/audio data to the remote site via HTTP server 140 and router 100. In the alternative, the video server 160 may receive a request for a training video from a remote site via the Internet through a firewall 138'. In the latter case, the video/audio data is sent by the video server to the remote site via the Internet. In the illustrated embodiment, processing system 84 also includes a license server 144 which is coupled to a license database 146 for storing, updating and verifying the status of diagnostic system service subscriptions. Alternatively, license server 144 may be placed outside of firewall 138 to verify subscription status prior to admission to the service facility.

Handling of service requests, messaging, and reporting is coordinated by a scheduler module 148 coupled to HTTP server 140. Scheduler module 148 coordinates activities of other servers comprising the processing system, such as a report server 150, a message server 152, and a software download server 154. As will be appreciated by those skilled in the art, servers 150, 152 and 154 are coupled to memory devices (not shown) for storing data such as task lists, addresses, log files, message and report files, applications software, etc. In particular, as illustrated in FIG. 4, software server 154 is coupled via one or more data channels to a storage device 156 for containing transmittable software packages which may be sent directly to the diagnostic systems, accessed by the diagnostic systems, or supplied on pay-per-use or purchase basis. Message and report servers 152 and 154 are further coupled, along with communications module 104, to a delivery handling module 158, which is configured to receive outgoing messages, ensure proper connectivity with diagnostic systems, and coordinate transmission of messages to the diagnostic systems and the transmission of messages and task lists to remotely located field engineers via the network.

In a preferred embodiment, the foregoing functional circuitry may be configured as hardware, firmware, or software on any appropriate computer platform. For example, the functional circuitry of the diagnostic systems may be programmed as appropriate code in a personal computer or workstation, either incorporated entirely in or added to the system scanner. The functional circuitry of the service facility may include additional personal computers or workstations, in addition to a main frame computer in which one or more of the servers, the scheduler, etc., are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of service data between the diagnostic systems and a central service facility, which is preferably implemented in an interactive manner to provide regular updates to the diagnostic systems of service activities.

Figure 5:
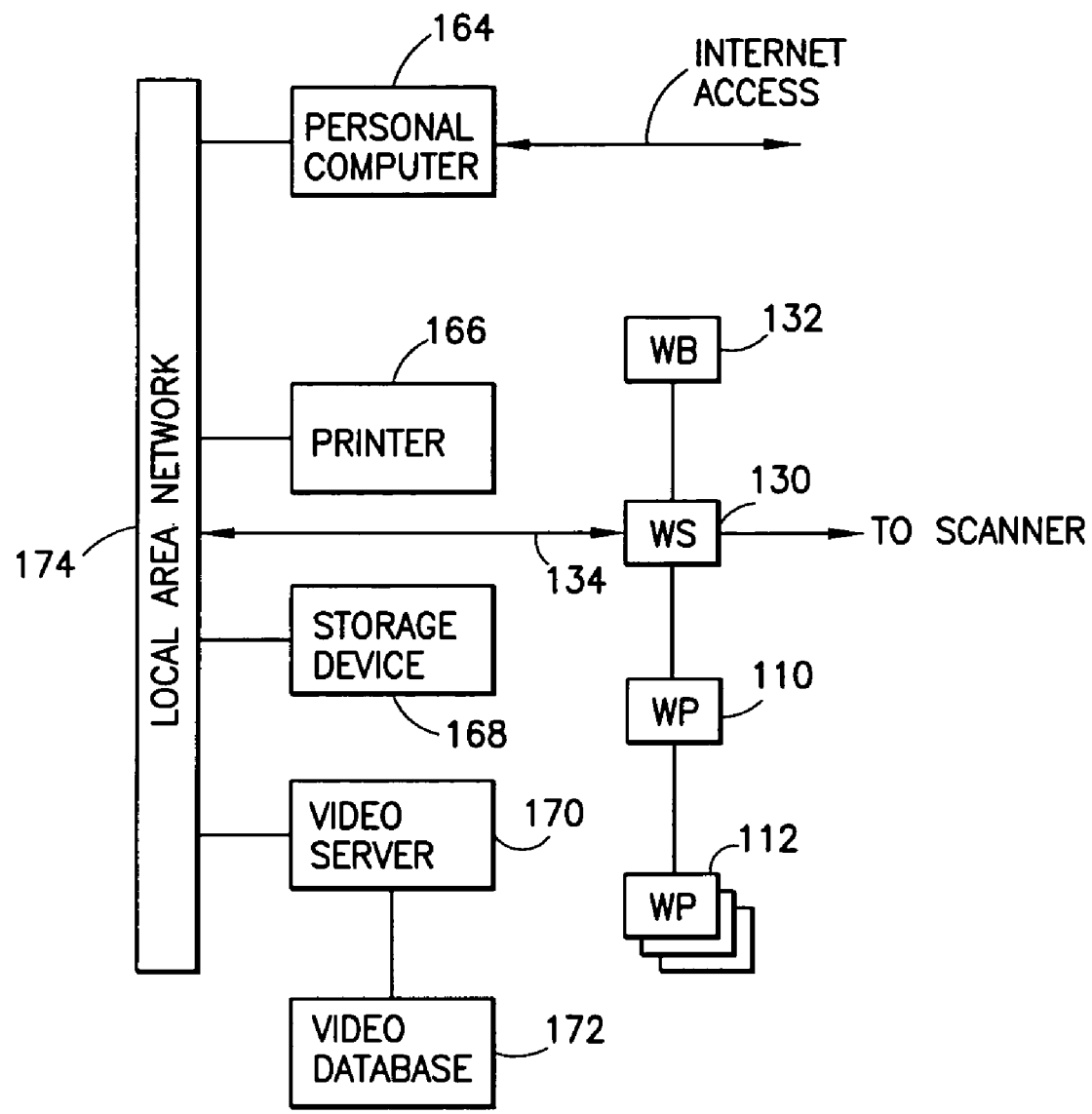
FIG. 5 is a block diagram of a portion of a local area network at a remote medical facility in accordance with a preferred embodiment of the invention.

Referring to FIG. 5, the diagnostic system at a remote facility may be connected to other equipment at that remote facility via a local area network (LAN) 174. As previously described, a direct network connection 134 may be provided between the web server 130 of the diagnostic system and the LAN 174. The LAN 174 enables the diagnostic to communication with other networked equipment, such as a printer 166 and a storage device 168. In accordance with an alternative preferred embodiment of the invention, a video server 170 located at the remote facility is connected to the LAN 174. Like video server 160 (see FIG. 4) at the central service facility, video server 170 is configured to address requests for training videos. In response to a request for a training video from an end-user received via the LAN 174, the video server 170 retrieves the video/audio data for the requested video from a video database 172 stored at the remote facility and transmits that video/audio data to the remote site via the LAN 174.

In accordance with a further preferred embodiment of the invention, a training video may be requested from a personal computer (workstation) 164 at the remote facility and then view at that workstation. The training video may be selected and viewed by connecting to a video server 170 at the remote facility via the LAN 174, or by connecting to a video server 160 (see FIG. 4) at the central service facility via the Internet.

As described above, the diagnostic systems and associated workstations facilitate interfacing with the central service facility via a series of interactive user-viewable pages.

Figure 6:
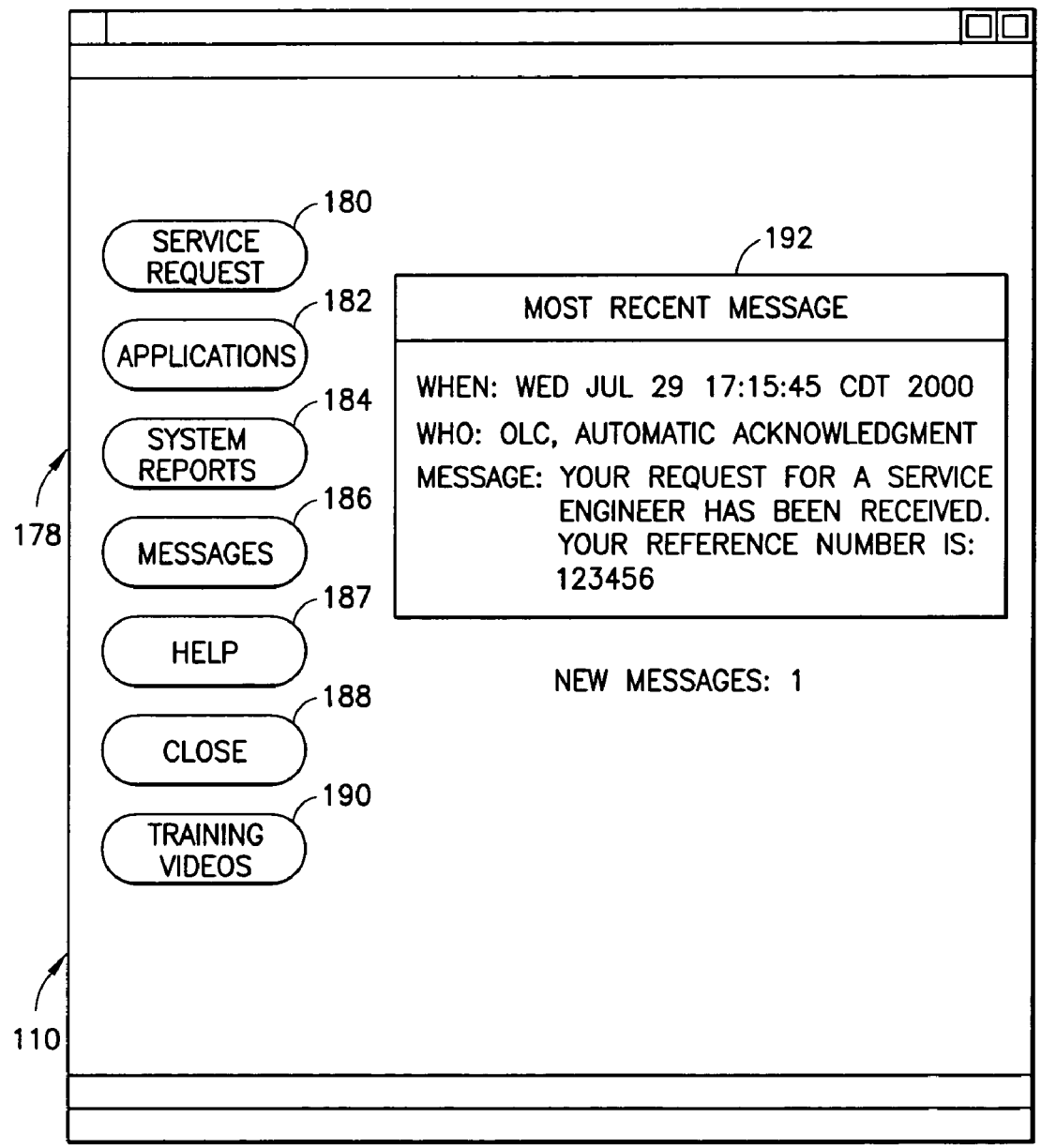
FIG. 6 is an exemplary user interface page incorporated in the remote diagnostic system (or workstation) for sending and receiving service data between the diagnostic system and a central service facility and for sending instructional information from the central facility to the remote diagnostic system.

FIG. 6 illustrates an exemplary main web page which presents the main menu for selecting a desired interactive mode, e.g., composing service requests and task lists, selecting and transferring messages, reports and diagnostic system software, etc. It should be noted that through the following discussion, reference is made to viewable pages for interfacing in the language of the present description. However, in a preferred embodiment, the platform may be configured to present such interface pages in several different languages, depending upon the country in which the system is installed.

As illustrated first in FIG. 6, a main web page 110 is accessible from a normal diagnostic system screen viewable on a diagnostic system monitor (e.g., monitors 36, 52 or 66). The main web page 110 may therefore be viewable by clicking an input device such as a mouse on an icon (not shown) on the normal operational screen. Main web page 110 includes a menu 178 of navigation devices in the form of graphical (i.e., virtual) buttons for accessing other interface pages in the graphical user interface. In the illustrated embodiment, these graphical devices include a service request button 180 for accessing a service request page, an applications button 182 for accessing an applications page, a system reports button 184 for accessing service reports, a messages button 186 for sending and receiving interactive service messages, and a training video button 190 for accessing a training video. A help button 187 is provided for accessing user information, help topics etc., which may be resident on the system, or available through on-line sources viewable through the system browser. A close or exit button 188 is provided for returning to the normal scanner interface page. In addition to these navigational devices, main page 110 includes a message area 192 in which information regarding the most recent messages is displayed. This information may include identification of the time and date received, the originator of the message, and a brief summary of the message content or title. Thus, upon accessing main page 110, the system user is made aware of service activities carried out by the central service facility or field service engineer.

Figure 7:
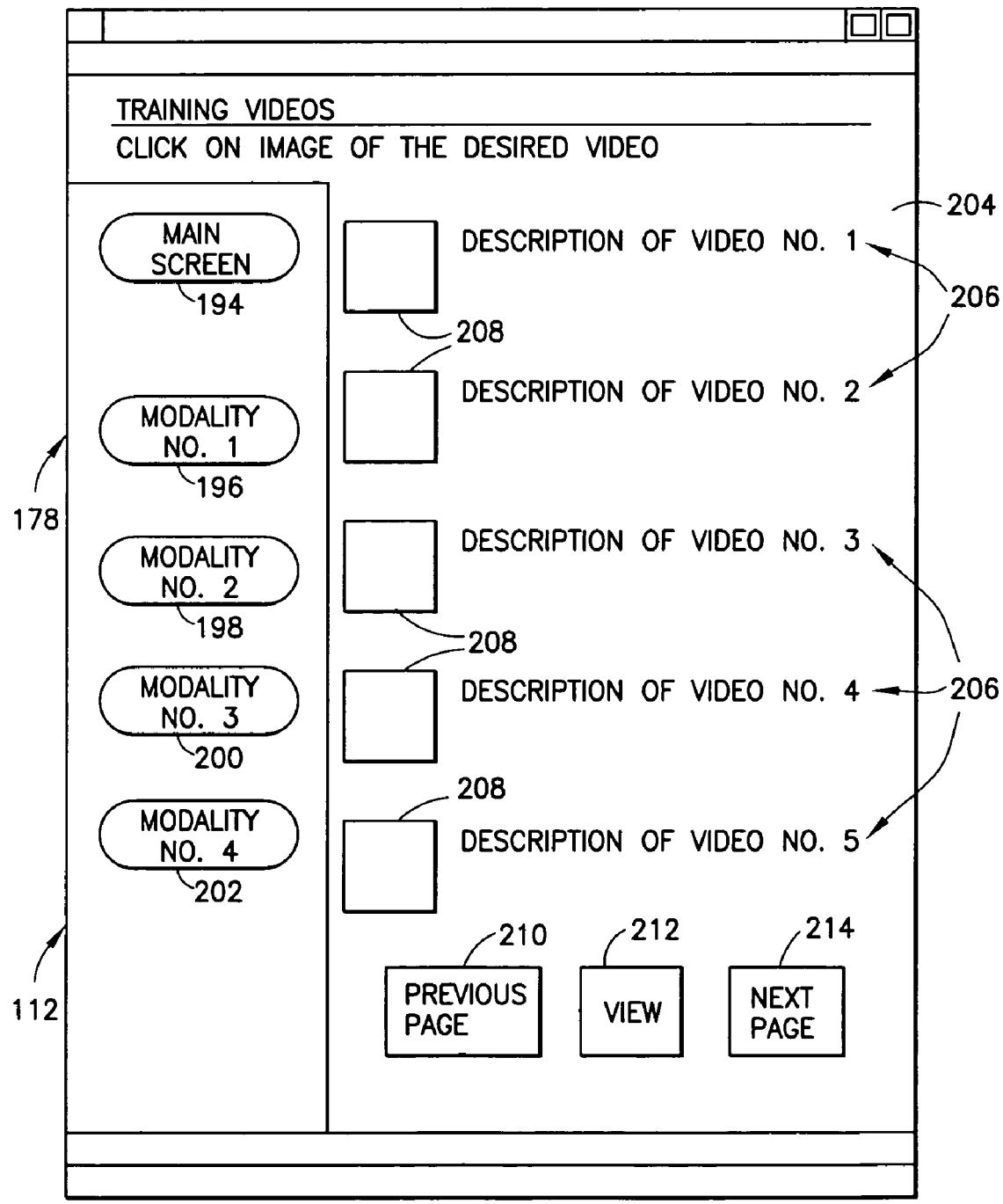
FIG. 7 is a second user interface page for formulating and sending a request for a training video from a scanner operator to a central service facility in accordance with the preferred embodiment of the invention.

FIG. 7 illustrates a training video web page 112 accessed by actuation of the training video button 190 on the main web page (see FIG. 6). The training video web page 112 includes a main menu button 194 for returning to the main web page shown in FIG. 6. As mentioned above, the uniform graphical user interface facilitates formulation of training video requests and enables system designers to permit accessing of a central video library in a similar manner across several diagnostic system modalities.

As seen in FIG. 7, the training video web page 112 is formatted to provide a graphical user interface for searching and selecting a training video from the video library. Preferably the videos in the library are classified by imaging modality. Accordingly, the training video web page has a menu 178 for selecting a desired imaging modality, a respective virtual modality selection button being provided for each imaging modality. For the purpose of illustration, FIG. 7 shows four virtual modality selection buttons 196, 198, 200, and 202 corresponding to modalities Nos. 1-4 respectively. Exemplary modalities include CT, MRI and PET systems, x-ray systems, ultrasound imaging systems, nuclear medicine systems, etc. Each virtual modality selection button preferably takes the form of a virtual toggle switch which the end-user can toggle on and off by superimposing a cursor on the graphical representation of the button and then double-clicking in a well-known manner, using a mouse or other user input device. Other well-known methods of making a selection on a graphical interface can also be utilized, e.g., highlighting the modality identifier on the screen and then clicking on a Select button. Optionally, each virtual modality selection button Optionally, each virtual video selection button may have a condensed image or thumbnail sketch symbolizing a respective imaging modality superimposed thereon.

In response to selection of an imaging modality, the first page of a list of available training videos relating to the selected modality is displayed on the user-viewable page 112. A first page of an exemplary list is generally depicted in FIG. 7. A series of training videos are listed within a text area 204. For each training video provided in the listing, a brief description of the subject matter of the training video is provided as indicated at reference numerals 206. Each entry on the list also includes a respective virtual video selection button 208. Optionally, each virtual video selection button may have a condensed image or thumbnail sketch symbolizing the subject matter of the respective training video 208 superimposed thereon. Prior to selection, the end-user can scroll through the list of videos relating to the selected imaging modality by clicking on the Previous Page button 210 and Next Page button 214 in a well-known manner. Other buttons, such as First Page and Last Page buttons, may also be included. Training videos may be added to the listing from time to time, such as by downloading from the service facility.

A training video corresponding to an entry on the displayed page can be selected by clicking on the corresponding virtual video selection button 208 and then clicking on a virtual View button 212 displayed on the web page. Some of the training videos may be made available on a fee-per-use, one-time payment, or a license basis. The web server included in the uniform interactive platform includes unique system identification data which supplements the information input by the user. The unique system identification data is automatically sent to the service center along with the request to view a training video.

Referring back to FIG. 2, the request to view a training video and source system identifier are transmitted from the diagnostic system 12 to the service center 22 via the network 80. If the identified source system making the request has a valid subscription, the request to view a training video is approved by the service center 22 and the requested training video is downloaded by the service center to the source system via the network 80.

Referring to FIG. 4, the HTTP applications server 140 receives information from the license module 144 that the end-user at the remote facility is licensed to access the requested training video and then passes the request for training video on to the video server 160. The video server 160 is programmed with the capability to retrieve the requested training video from a video database or library 162. The video server 160 then sends the training video to the remote location via the delivery handling module 158, router 100, a modem 98 and network 80. The training video can be downloaded to a memory at the remote diagnostic system or workstation for subsequent viewing by the end-user. Alternatively, the training video can be streamed to the remote diagnostic system or workstation for viewing in real-time.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "diagnostic system" includes diagnostic systems, imaging systems and associated workstations.

The invention claimed is:

1. A system comprising a central service facility connected to a remotely located medical diagnostic imaging system of a particular imaging modality via a network, wherein said central service facility comprises a memory that stores a video library comprising a multiplicity of training videos, each training video being classified as a member of one of a plurality of training video classes, each class corresponding to a respective imaging modality, said particular imaging modality belonging to a first training video class, and each training video showing one or more of the following: how to operate a medical diagnostic imaging system of said respective imaging modality, how to perform an examination of a particular exam type on a patient using a medical diagnostic imaging system of said respective imaging modality or how to make a diagnosis during an examination of said particular exam type performed using a medical diagnostic imaging system of said respective imaging modality;

wherein said remotely located medical diagnostic imaging system comprises a display monitor and a web browser for displaying interactive web pages on said display monitor, said web browser being programmed to display a first interactive web page comprising a plurality of operational mode graphical buttons, only one of which is useable for navigating to a second interactive web page to be displayed on said display monitor; to display said second interactive web page on said display monitor in response to selection of said one operational mode graphical button, said second interactive web page comprising a plurality of imaging modality graphical buttons each of which corresponds to a respective one of said plurality of training video classes, including a first imaging modality graphical button corresponding to said first training video class; and to display an updated version of said second interactive web page on said display monitor in response to clicking on said first imaging modality graphical button, said updated version of said second interactive web page comprising a plurality of training video graphical buttons each of which corresponds to a respective one of a plurality of training videos belonging to said first imaging modality class;

wherein said remotely located medical diagnostic imaging system further comprises means for sending a training video request to said central service facility via said network in response to selection of a training video belonging to said first imaging modality class by clicking on one of said plurality of training video graphical buttons displayed on said display monitor, said training video request comprising an identifier identifying said selected training video and a source system identifier identifying said medical diagnostic imaging system;

wherein said central service facility further comprises: means for verifying whether the medical diagnostic imaging system identified by said source system identifier has a valid subscription in response to receipt of said training video request and said source system identifier; means for retrieving video and audio data of said selected training video from said video library following receipt of said training video request at said central service facility only if the medical diagnostic imaging system identified by said source system identifier has a valid subscription; and means for sending said video and audio data of said selected training video from said central service facility to said medical diagnostic imaging system via said network; and wherein said remotely located medical diagnostic imaging system further comprises: means for displaying said video data on said display monitor; and means for displaying a diagnostic image of a portion of the anatomy of a patient on said display monitor during an examination of said particular exam type on said patient.

2. The system as recited in claim 1, wherein said medical diagnostic imaging system further comprises an audio speaker and a video/audio player for displaying said video data on said display screen and outputting said audio data to said audio speaker.

3. The system as recited in claim 1, wherein said central service facility further comprises:

a license server programmed to verify whether the medical diagnostic imaging system identified by said source system identifier has a valid subscription in response to receipt of said training video request at said central service facility; and an application server coupled to said license server and programmed to decline said training video request if said license server communicates that the medical diagnostic imaging system identified by said source system identifier does not have a valid subscription.

4. A method for operating a system comprising a central service facility connected to a remotely located medical diagnostic imaging system of a particular imaging modality via a network, comprising the steps of:

storing a multiplicity of training videos in a video library, each training video being classified as a member of one of a plurality of training video classes, each class corresponding to a respective imaging modality, said particular imaging modality belonging to a first training video class, and each training video showing one or more of the following: how to operate a medical diagnostic imaging system of said respective imaging modality, how to perform an examination of a particular exam type on a patient using a medical diagnostic imaging system of said respective imaging modality or how to make a diagnosis during an examination of said particular exam type performed using a medical diagnostic imaging system of said respective imaging modality;

displaying a first interactive web page on a display monitor of said remotely located medical diagnostic imaging system of said particular imaging modality, said first interactive web page comprising a plurality of operational mode graphical buttons, only one of which is useable for navigating to a second interactive web page to be displayed on said display monitor;

displaying said second interactive web page on said display monitor in response to selection of said one operational mode graphical button, said second interactive web page comprising a plurality of imaging modality graphical buttons each of which corresponds to a respective one of said plurality of training video classes, including a first imaging modality graphical button corresponding to said first training video class;

displaying an updated version of said second interactive web page on said display monitor in response to clicking on said first imaging modality graphical button, said updated version of said second interactive web page comprising a plurality of training video graphical buttons each of which corresponds to a respective one of a plurality of training videos belonging to said first imaging modality class;

selecting a training video belonging to said first imaging modality class by clicking on one of said plurality of training video graphical buttons being displayed on said display monitor;

sending a training video request from said medical diagnostic imaging system to said central service facility via said network, said training video request comprising an identifier identifying said selected training video and a source system identifier identifying said medical diagnostic imaging system;

in response to receipt of said training video request and said source system identifier at said central service facility, verifying whether the medical diagnostic imaging system identified by said source system identifier has a valid subscription;

retrieving video and audio data of said selected training video from said video library following receipt of said training video request at said central service facility only if the medical diagnostic imaging system identified by said source system identifier has a valid subscription;

sending said video and audio data of said selected training video from said central service facility to said medical diagnostic imaging system via said network;

displaying said video data on said display monitor of said medical diagnostic imaging system;

viewing said displayed video data;

subsequent to said viewing step, performing an examination of said particular exam type on a patient using said medical diagnostic imaging system, said viewing step and said examination of said particular exam type being performed by the same person; and during said examination, displaying a diagnostic image of a portion of the anatomy of said patient on said display monitor.

5. A system comprising a video server connected to a remotely located medical diagnostic imaging system of a particular imaging modality via a network, wherein said video server has access to a video library comprising a multiplicity of training videos, each training video being classified as a member of one of a plurality of training video classes, each class corresponding to a respective imaging modality, said particular imaging modality belonging to a first training video class, and each training video showing one or more of the following: how to operate a medical diagnostic imaging system of said respective imaging modality, how to perform an examination of a particular exam type on a patient using a medical diagnostic imaging system of said respective imaging modality or how to make a diagnosis during an examination of said particular exam type performed using a medical diagnostic imaging system of said respective imaging modality;

wherein said remotely located medical diagnostic imaging system comprises a display monitor and a web browser for displaying interactive web pages on said display monitor, said web browser being programmed to display a first interactive web page comprising a plurality of operational mode graphical buttons, only one of which is useable for navigating to a second interactive web page to be displayed on said display monitor; to display said second interactive web page on said display monitor in response to selection of said one operational mode graphical button, said second interactive web page comprising a plurality of imaging modality graphical buttons each of which corresponds to a respective one of said plurality of training video classes, including a first imaging modality graphical button corresponding to said first training video class; and to display an updated version of said second interactive web page on said display monitor in response to clicking on said first imaging modality graphical button, said updated version of said second interactive web page comprising a plurality of training video graphical buttons each of which corresponds to a respective one of a plurality of training videos belonging to said first imaging modality class;

wherein said remotely located medical diagnostic imaging system further comprises means for sending a training video request to said video server via said network in response to selection of a training video belonging to said first imaging modality class by clicking on one of said plurality of training video graphical buttons displayed on said display monitor, said training video request comprising an identifier identifying said selected training video;

wherein said video server comprises: means for retrieving video and audio data of said selected training video from said video library following receipt of said training video request; and means for sending said video and audio data of said selected training video to said medical diagnostic imaging system via said network; and wherein said remotely located medical diagnostic imaging system further comprises: means for displaying said video data on said display monitor; and means for displaying a diagnostic image of a portion of the anatomy of a patient on said display monitor during an examination of said particular exam type on said patient.

\* \* \* \* \*